United States Patent [19]

Thummel et al.

[11] Patent Number: 4,555,262
[45] Date of Patent: Nov. 26, 1985

[54] N-AZIDOPHENYLSULFONYL-N'-PYRIMIDINYL UREAS

[75] Inventors: Rudolph C. Thummel, Courgenay; Werner Föry, Basel, both of Switzerland

[73] Assignee: Ciba-Geigy Corporation, Ardsley, N.Y.

[21] Appl. No.: 525,365

[22] Filed: Aug. 22, 1983

[30] Foreign Application Priority Data

Sep. 1, 1982 [CH] Switzerland .......................... 5196/82

[51] Int. Cl.$^4$ .................. A01N 47/36; C07D 239/46; C07D 251/16
[52] U.S. Cl. ........................................ 71/92; 544/209; 544/212; 544/321; 544/324; 544/331; 71/93
[58] Field of Search .................... 544/321, 324, 331; 71/92

[56] References Cited

FOREIGN PATENT DOCUMENTS 0001515 4/1979 European Pat. Off. ................ 71/92
102924 3/1984 European Pat. Off. ................ 71/92

Primary Examiner—Robert Gerstl
Attorney, Agent, or Firm—Edward McC. Roberts; Frederick H. Rabin

[57] ABSTRACT

The invention relates to N-azidophenylsulfonyl-N'-pyrimidinyl- and -N'-triazinylureas of the general formula

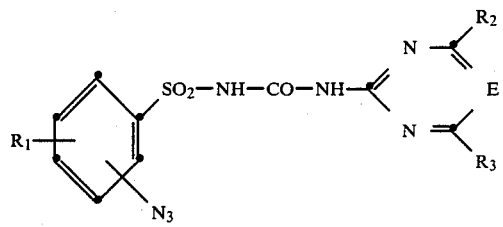

wherein
E is nitrogen or the methine bridge,
$R_1$ is hydrogen, halogen, nitro, $C_1$–$C_4$alkyl, $C_1$–$C_4$haloalkyl, $C_1$–$C_4$alkoxy, $C_1$–$C_4$haloalkoxy, $C_1$–$C_4$alkoxycarbonyl, $C_1$–$C_4$alkylthio, $C_1$–$C_4$alkylsulfinyl, $C_1$–$C_4$alkylsulfonyl or $C_2$–$C_5$alkoxyalkoxy,
$R_2$ is $C_1$–$C_3$alkyl, $C_1$–$C_3$alkoxy or $C_1$–$C_3$haloalkoxy,
$R_3$ is hydrogen, halogen, $C_1$–$C_3$alkyl, $C_1$–$C_3$haloalkyl, $C_1$–$C_3$alkoxy, $C_1$–$C_3$haloalkoxy, $C_2$–$C_5$alkoxyalkoxy or —$NR_4R_5$, wherein
$R_4$ is hydrogen or methyl and
$R_5$ is hydrogen, methyl, ethyl or methoxy
and to the salts thereof with amines, alkali metal hydroxides and alkaline earth metal hydroxides or with quaternary ammonium bases. These compounds have good pre- and postemergence selective herbicidal and growth regulating properties.

20 Claims, No Drawings

N-AZIDOPHENYLSULFONYL-N'-PYRIMIDINYL UREAS

The present invention relates to novel N-azidophenylsulfonyl-N'-pyrimidinyl- and -N'-triazinylureas having herbicidal and growth regulating properties, to the preparation thereof, to compositions containing them, and to the use thereof for controlling weeds, in particular selectively, in crops of useful plants, or for regulating and inhibiting plant growth. The invention also relates to azidophenylsulfonamides prepared as intermediates for the synthesis of the novel compounds.

The N-azidophenylsulfonyl-N'-pyrimidinyl- and -N'-triazinylureas, and the salts thereof, have the general formula I

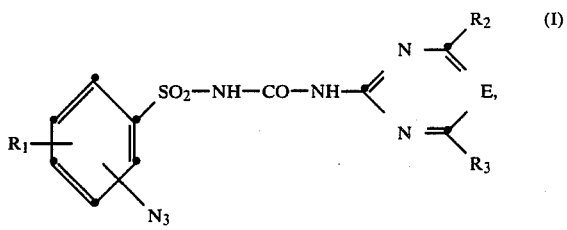

wherein
E is nitrogen or the methine bridge,
$R_1$ is hydrogen, halogen, nitro, $C_1$–$C_4$alkyl, $C_1$–$C_4$haloalkyl, $C_1$–$C_4$alkoxy, $C_1$–$C_4$haloalkoxy, $C_1$–$C_4$alkoxycarbonyl, $C_1$–$C_4$alkylthio, $C_1$–$C_4$alkylsulfinyl, $C_1$–$C_4$alkylsulfonyl or $C_2$–$C_5$alkoxyalkoxy,
$R_2$ is $C_1$–$C_3$alkyl, $C_1$–$C_3$alkoxy or $C_1$–$C_3$haloalkoxy,
$R_3$ is hydrogen, halogen, $C_1$–$C_3$alkyl, $C_1$–$C_3$haloalkyl, $C_1$–$C_3$alkoxy, $C_1$–$C_3$haloalkoxy, $C_2$–$C_5$alkoxyalkoxy or —$NR_4R_5$, wherein
$R_4$ is hydrogen or methyl and
$R_5$ is hydrogen, methyl, ethyl or methoxy.

Herbicidally active ureas, triazines and pyrimidines are generally known in the art. Arylsulfamoylheterocyclylaminocarbamoyl compounds with herbicidal and plant growth-regulating action have recently been described e.g. in European patent application 1515.

In the above definitions, alkyl denotes straight-chain or branched alkyl, e.g. methyl, ethyl, n-propyl, isopropyl, or the four butyl isomers.

Alkoxy denotes methoxy, ethoxy, n-propoxy, isopropoxy and the four butoxy isomers, with methoxy, ethoxy, or isopropoxy being preferred.

Alkylthio is e.g. methylthio, ethylthio, n-propylthio, isopropylthio and n-butylthio, with methylthio and ethylthio being preferred.

Alkylsulfinyl is e.g. methylsulfinyl, ethylsulfinyl, n-propylsulfinyl and n-butylsulfinyl. Preferred identities are methylsulfinyl and ethylsulfinyl.

Alkylsulfonyl is e.g. methylsulfonyl, ethylsulfonyl or n-propylsulfonyl. Preferred identities are methylsulfonyl and ethylsulfonyl.

Halogen in the above definitions, as well as moiety of haloalkyl and haloalkoxy is fluorine, chlorine and bromine, with fluorine and chlorine being preferred.

Accordingly, haloalkyl or haloalkyl moieties of the substituents defined above will be understood as comprising: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, with fluoromethyl, chloromethyl, difluoromethyl and trifluoromethyl being the preferred identities.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which either
(a) the azido radical is in the 2-position to the sulfonyl group, or
(b) $R_1$ is hydrogen, or
(c) $R_2$ and $R_3$ together contain not more than 3 carbon atoms, or
(d) $R_2$ and $R_3$ are selected from the group consisting of methyl, methoxy, dimethylamino, difluoromethoxy and 2,2,2-trifluoroethoxy, or
(e) $R_1$ is $C_1$–$C_4$alkoxycarbonyl.

A further preferred subgroup of compounds of formula I comprises those compounds in which $R_1$ is in the 2-position to the sulfonyl group and is $C_1$–$C_4$alkoxycarbonyl and $R_2$ and $R_3$ are selected from the group consisting of methyl, methoxy, difluoromethoxy, dimethylamino and 2,2,2-trifluoroethoxy and together contain not more than 3 carbon atoms.

Preferred compounds belonging to this group are the compounds of formula I, wherein $R_2$ and $R_3$ are methyl, methoxy or difluoromethoxy.

Preferred individual compounds are:
N-(2-azidophenylsulfonyl)-N'-(4-methoxy-6-methyl-1,3,5-triazin-2-yl)-urea,
N-(2-methoxycarbonyl-5-azidophenylsulfonyl)-N'-(4-difluoromethoxy-6-methylpyrimidin-2-yl)urea and
N-(2-azidophenylsulfonyl)-N'-(4-methoxy-6-methylpyrimidin-2-yl)urea.

The process for the preparation of the compounds of formula I is normally carried out in an inert organic solvent.

A first process for the preparation of compounds of formula I comprises reacting an azidophenylsulfonamide of the formula II

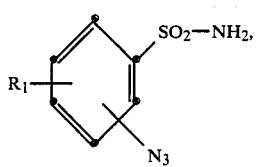 (II)

wherein $R_1$ is as defined for formula I, with an N-pyrimidinyl- or N-triazinylcarbamate of the formula III

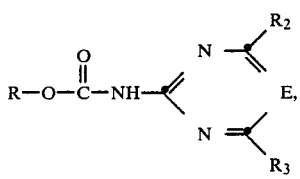 (III)

wherein E, $R_2$ and $R_3$ are as defined for formula I and R is phenyl, alkyl or substituted phenyl, in the presence of a base.

A second process for obtaining compounds of formula I comprises reacting an azidophenylsulfonylisocyanate of the formula IV

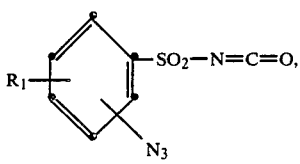 (IV)

wherein $R_1$ is as defined for formula I, with an amine of the formula V

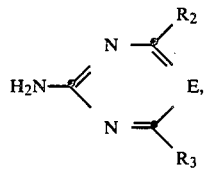 (V)

wherein $R_2$ and $R_3$ are as defined for formula I, optionally in the presence of a base.

The compounds of formula I may also be obtained by reacting an N-azidophenylsulfonylcarbamate of the formula VI

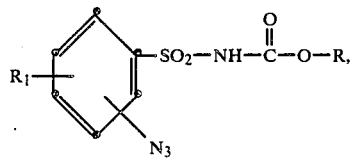 (VI)

wherein $R_1$ is as defined for formula I and R is phenyl, alkyl or substituted phenyl, with an amine of the formula V above.

Finally, the compounds of formula I are also obtained by diazotising an aminosulfonylurea of the formula VII

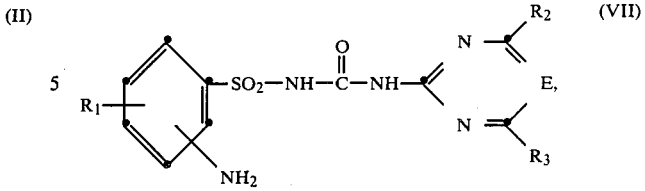 (VII)

wherein E, $R_1$, $R_2$ and $R_3$ are as defined for formula I, and introducing the azido group in known manner.

If desired, the ureas of formula I can be converted into addition salts with amines, alkali metal hydroxides or alkaline earth metal hydroxides or with quaternary ammonium bases. This conversion is carried out for example by reacting the compounds of formula I with the equimolar amount of a base and removing the solvent by evaporation.

The starting compounds of the formulae III, V and VII are known or they may be prepared by known methods.

Novel fluoroalkoxyaminopyrimidines and fluoroalkoxyaminotriazines of the formula V and the preparation thereof, as well as the preparation of corresponding compounds of formula II, are described in European patent application 70 804.

The novel compounds of the formulae IV and VI are prepared by known methods from the azidophenylsulfonamides of the formula II. The compounds have been specially developed for the synthesis of the compounds of formula I and therefore constitute an object of the invention.

Some of the azidophenylsulfonamides of the formula II are known [reference is made in this connection to Monatshefte der Chemie, 81, 970–980 (1950)].

The novel azidophenylsulfonamides of the formula II as well as the intermediates of the formulae IV and VI have been specially developed for the synthesis of the compounds of formula I and therefore also constitute a further object of the invention. The novel azidophenylsulfonamides have the general formula IIa

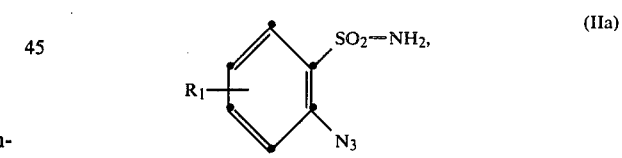 (IIa)

wherein $R_1$ is as defined for formula I.

The compounds of formula IIa are normally obtained by reducing analogous nitrophenylsulfonamides to the amino compounds by known methods, for example by catalytic reduction with combinations of metals and acids, by reduction with amalgams and aqueous alcohols or by reduction with alkali metal sulfides, and diazotising the amino compounds in known manner and converting the resultant diazonium salts into the azido compounds of the formula IIa.

Similar processes are described for example in Monatshefte der Chemie, 81, 970–980 (1950) or in Houben-Weyl, Methoden der organischen Chemie, 4th edition, Vol. 10/3, 781–836.

The intermediates of formula VII can be obtained in similar manner from corresponding nitrophenylsulfonylureas by reduction. Such nitrophenylsulfonylureas are either known or obtained by known methods.

It is convenient to carry out the reactions for obtaining compounds of formula I in aprotic, inert organic solvents such as methylene chloride, tetrahydrofuran, acetonitrile, dioxan, or toluene.

The reaction temperatures are preferably in the range from $-20°$ C. to $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The compounds of formula I are stable compounds and no protective measures are required for handling them.

When used in low rates of application, the compounds of formula I have good selective growth inhibiting and selective herbicidal properties which make them most suitable for use in crops of useful plants, especially in sugar cane, cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

The compounds of formula I have pronounced growth-regulating properties which can result in an increase in the yield of cultivated plants or harvested crops. In addition, many compounds of formula I have a growth inhibiting action which is dependent on the concentration. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanisms of yield increase using growth regulators resides in the fact that nutrients are able increasingly to promote flower formation and druiting, whilst vegetative growth is inhibited.

Inhibition of the vegetative growth of monocot plants, e.g. grasses or also cultivated plants such as cereals, is sometimes desirable and advantageous. Such a growth inhibition is of economic interest, inter alia, in respect of grasses, as the frequency of cutting in flower gardens, parks, sport fields or road shoulders can thereby be reduced. Of importance too is the inhibition of growth of herbaceous and ligneous plants on road shoulders and near transmission lines, or quite generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging. Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic)hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in H. Stache, "Tensid-Taschenbuch", 2nd. edition, C. Hanser Verlag, Munich and Vienna, 1981, and M+J. Ash, "Encyclopedia of Surfactants", Vol. I-III, Chemical Publishing Co. New York, 1980–81.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):
Emulsifiable concentrates
active ingredient: 1 to 20%, preferably 5 to 10%
surfactant: 5 to 30%, preferably 10 to 20%
liquid carrier: 50 to 94%, preferably 70 to 85%
Dusts
active ingredient: 0.1 to 10%, preferably 0.1 to 1%
solid carrier: 99.9 to 90%, preferably 99.9 to 99%
Suspension concentrates
active ingredient: 5 to 75%, preferably 10 to 50%
water: 94 to 25%, preferably 90 to 30%
surfactant: 1 to 40%, preferably 2 to 30%
Wettable powders
active ingredient: 0.5 to 90%, preferably 10 to 80%
surfactant: 0.5 to 20%, preferably 1 to 15%
solid carrier: 5 to 95%, preferably 15 to 90%
Granulates
active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers as well as fertilisers and other compounds for obtaining special effects.

The invention is illustrated by the following Examples.

EXAMPLE 1

N-(2-azidophenylsulfonyl)-N'-(4-methoxy-6-methyl-1,3,5-triazin-2-yl)urea

A solution of 1 g of sodium nitrite in 4 ml of water is slowly added dropwise at 0°–5° C. to a mixture of 3.4 g of N-(2-aminophenylsulfonyl)-N'-(4-methoxy-6-methyl-1,3,5-triazin-2-yl)urea, 10 g of ice and 4 ml of 36% hydrochloric acid. After the reaction mixture has been stirred for 2 hours at 0° C., a solution of 1 g of sodium azide in 4 ml of water is added dropwise and the temperature is allowed to rise to 20° C. The reaction mixture is extracted with three 20 ml portions of methylene chloride. The combined organic phases are dried and concentrated. Recrystallisation of the residue yields 1.0 g of N-(2-azidophenylsulfonyl)-N'-(4-methoxy-6-methyl-1,3,5-triazin-2-yl)urea which decomposes at 175° C.

EXAMPLE 2

N-(2-azidophenylsulfonyl)-N'-(4,6-dimethoxypyrimidin-2-yl)-urea.

A solution of 1.0 g of sodium nitrite in 4 ml of water is added slowly dropwise at 0°–5° C. to a mixture of 3.5 g of N-(2-aminophenylsulfonyl)-N'-dimethoxypyrimidin-2-yl)urea, 10 g of ice and 4 ml of 36% hydrochlorice acid. After the reaction mixture has been stirred for 2 hours at 0° C., a solution of 1 g of sodium azide in 4 ml of water is added dropwise and the temperature is allowed to rise to 20° C. The reaction mixture is extracted with three 20 ml portions of methylene chloride. The combined organic phases are dried and concentrated. Recrystallisation of the residue yields 0.52 g of N-(2-azidophenylsulfonyl)-N'-(4,6-dimethoxypyrimidin-2-yl)urea which decomposes at 190° C.

EXAMPLE 3

N-(2-azidophenylsulfonyl)-N'-(4-methoxy-6-methylpyrimidin-2-yl)urea

A solution of 1.0 g of sodium nitrite in 4 ml of water is added slowly dropwise at 0°–5° C. to a mixture of 3.4 g of N-(2-aminophenylsulfonyl)-N'-4-methoxy-6-methylpyrimidin-2-yl)urea, 10 g of ice and 4 ml of 36% hydrochloric acid. After the reaction mixture has been stirred for 2 hours at 0° C. a solution of 1 g of sodium azide in 4 ml of water is added dropwise and the temperature is allowed to rise to 20° C. The reaction mixture is extracted with three 20 ml portions of methylene chloride. The combined organic phases are dried and concentrated. Recrystallisation of the residue yields 0.85 g of N-(2-azidophenylsulfonyl)-N'-(4-methoxy-6-methylpyrimidin-2-yl)urea which decomposes at 178°–179° C.

EXAMPLE 4

N-(4-azidophenylsulfonyl)-N'-(4-methoxy-6-methylpyrimidin-2-yl)urea

A solution of 2.9 g of N-(4-methoxy-6-methylpyrimidin-2-yl)phenylcarbamate in 10 ml of dioxan is added dropwise at 20°–25° C. to a solution of 2 g of 4-azidophenylsulfonamide and 1.6 ml of 1,5-diazabicyclo(5,4,0)-undec-5-ene in 20 ml of dioxan and the mixture is stirred for 3 hours at the same temperature. The reaction mixture is then taken up in 200 ml of water and the aqueous mixture is then acidified with hydrochloric acid to pH 2. The precipitated product is isolated, washed with ethyl acetate and dried, affording N-(4-azidophenylsulfonyl)-N'-(4-methoxy-6-methylpyrimidin-2-yl)urea in 67% yield in the form of greenish crystals with a melting point of 192° C.

The intermediates and final products listed in the following tables are obtained in corresponding manner.

TABLE 1

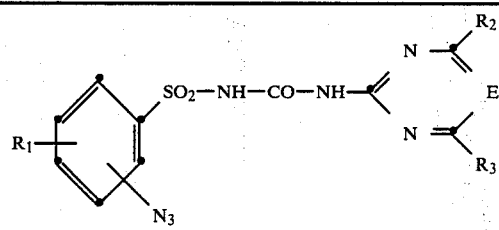

| No. | $R_1$ | Position of the azido group | $R_2$ | $R_3$ | E | Physical data |
|---|---|---|---|---|---|---|
| 1.1 | H | 2 | $CH_3$ | $OCH_3$ | N | m.p.:174° C. (decomp.) |
| 1.2 | H | 2 | $OCH_3$ | $OCH_3$ | N | |
| 1.3 | H | 2 | $OCH_3$ | $-N(CH_3)_2$ | N | |
| 1.4 | H | 2 | $OCH_3$ | $-OCH_2-CF_2$ | N | |
| 1.5 | H | 2 | $OCH_3$ | $OCH_3$ | CH | m.p.:190° C. (decomp.) |
| 1.6 | H | 2 | $CH_3$ | $OCH_3$ | CH | m.p.:178–179° (decomp.) |
| 1.7 | H | 2 | $CH_3$ | $CH_3$ | CH | |
| 1.8 | H | 2 | $CH_3$ | $OCHF_2$ | CH | |
| 1.9 | 4-$OCH_3$ | 3 | $CH_3$ | $OCH_3$ | N | |
| 1.10 | 4-$OCH_3$ | 3 | $CH_3$ | $OCH_3$ | CH | m.p.:177° C. (decomp.) |
| 1.11 | H | 3 | $CH_3$ | $OCH_3$ | N | |
| 1.12 | H | 3 | $CH_3$ | $OCH_3$ | CH | m.p.:190° C. (decomp.) |
| 1.13 | H | 4 | $CH_3$ | $OCH_3$ | N | |
| 1.14 | H | 4 | $CH_3$ | $OCH_3$ | CH | m.p.:192° C. (decomp.) |
| 1.15 | 2-$CH_3$ | 5 | $OCH_3$ | $CH_3$ | N | m.p.:170–173° |
| 1.16 | 6-Cl | 2 | $OCH_3$ | $CH_3$ | CH | m.p.:165° (decomp.) |
| 1.17 | 2-$COOCH_3$ | 5 | $CH_3$ | $OCH_3$ | N | |
| 1.18 | 2-$COOCH_3$ | 5 | $CH_3$ | $CH_3$ | N | |
| 1.19 | 2-$COOCH_3$ | 5 | $OCH_3$ | $OCH_3$ | N | |
| 1.20 | 2-$COOCH_3$ | 5 | $OCH_3$ | $N(CH_3)_2$ | N | |
| 1.21 | 2-$COOCH_3$ | 5 | $OCH_3$ | $OCH_2-CH_3$ | N | |
| 1.22 | 2-$COOCH_3$ | 5 | $OCH_3$ | $OCH_2-CF_3$ | N | |
| 1.23 | 2-$COOCH_3$ | 5 | $C_2H_5$ | $OCH_3$ | N | |
| 1.24 | 2-$COOCH_3$ | 5 | $OC_2H_5$ | $OC_2H_5$ | N | |
| 1.25 | 2-$COOCH_3$ | 5 | $CH_3$ | $CH_3$ | CH | |
| 1.26 | 2-$COOCH_3$ | 5 | $CH_3$ | $OCH_3$ | CH | |
| 1.27 | 2-$COOCH_3$ | 5 | $CH_3$ | $OCHF_2$ | CH | |
| 1.28 | 2-$COOCH_3$ | 5 | $OCH_3$ | $OCH_3$ | CH | |
| 1.29 | 2-$COOCH_3$ | 5 | $OCH_3$ | $OCHF_2$ | CH | |
| 1.30 | 2-$COOCH_3$ | 5 | $OCHF_2$ | $OCHF_2$ | CH | |
| 1.31 | 2-$COOCH_3$ | 5 | $OCH_3$ | Cl | CH | |
| 1.32 | 2-$COOCH_3$ | 5 | $OCH_3$ | F | CH | |
| 1.33 | 2-$COOCH_3$ | 5 | $OCH_2F$ | $OCH_2$ | CH | |
| 1.34 | 2-$COOCH_3$ | 5 | $OCH_3$ | $OCF_2-CHF_2$ | CH | |
| 1.35 | 2-$COOCH_3$ | 5 | $CH_3$ | $OCF_2-CHF_2$ | CH | |
| 1.36 | 2-$CH_3$ | 5 | $CH_3$ | $OCH_3$ | N | |
| 1.37 | 2-$CH_3$ | 5 | $CH_3$ | $CH_3$ | N | |
| 1.38 | 2-$CH_3$ | 5 | $OCH_3$ | $OCH_3$ | N | |
| 1.39 | 2-$CH_3$ | 5 | $OCH_3$ | $N(CH_3)_2$ | N | |

TABLE 1-continued

![structure]

| No. | $R_1$ | Position of the azido group | $R_2$ | $R_3$ | E | Physical data |
|---|---|---|---|---|---|---|
| 1.40 | 2-$CH_3$ | 5 | $OCH_3$ | $OCH_2$—$CH_3$ | N | |
| 1.41 | 2-$CH_3$ | 5 | $OCH_3$ | $OCH_2$—$CF_3$ | N | |
| 1.42 | 2-$CH_3$ | 5 | $C_2H_5$ | $OCH_3$ | N | |
| 1.43 | 2-$CH_3$ | 5 | $OC_2H_5$ | $OC_2H_5$ | N | |
| 1.44 | 2-$CH_3$ | 5 | $CH_3$ | $CH_3$ | CH | |
| 1.45 | 2-$CH_3$ | 5 | $CH_3$ | $OCH_3$ | CH | |
| 1.46 | 2-$CH_3$ | 5 | $CH_3$ | $OCHF_2$ | CH | |
| 1.47 | 2-$CH_3$ | 5 | $OCH_3$ | $OCH_3$ | CH | |
| 1.48 | 2-$CH_3$ | 5 | $OCH_3$ | $OCHF_2$ | CH | |
| 1.49 | 2-$CH_3$ | 5 | $OCHF_2$ | $OCHF_2$ | CH | |
| 1.50 | 2-$CH_3$ | 5 | $OCH_3$ | Cl | CH | |
| 1.51 | 2-$CH_3$ | 5 | $OCH_3$ | F | CH | |
| 1.52 | 2-$CH_3$ | 5 | $OCH_2F$ | $OCH_3$ | CH | |
| 1.53 | 2-$CH_3$ | 5 | $OCH_3$ | $OCF_2$—$CHF_2$ | CH | |
| 1.54 | 2-$CH_3$ | 5 | $CH_3$ | $OCF_2$—$CHF_2$ | CH | |

TABLE 2

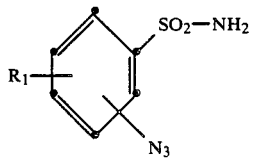

| No. | $R_1$ | Position of the azido group | Physical data |
|---|---|---|---|
| 2.1 | H | 3 | m.p.:128–129° C. |
| 2.2 | H | 4 | m.p.:118–119° C. |
| 2.3 | 4-$OCH_3$ | 3 | m.p.:128–130° C. |
| 2.4 | H | 2 | decomp. at 189° C. |
| 2.5 | 2-$CH_3$ | 5 | |
| 2.6 | 2-$COOCH_3$ | 5 | |

FORMULATION EXAMPLES

EXAMPLE 5

Formulation examples for compounds of formula I (percentages are by weight)

| (a) Wettable powders | (a) | (b) | (c) |
|---|---|---|---|
| compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of formula I | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Ready for use dusts are obtained by mixing the active ingredient with the carriers, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspension of any desired concentration can be obtained by dilution with water.

| (g) Salt solution | |
|---|---|
| compound of formula | 5% |
| isopropylamine | 1% |
| octylphenol polyethylene glycol ether (78 moles of ethylene oxide) | 3% |
| water | 91% |

BIOLOGICAL EXAMPLES

EXAMPLE 6

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20,000 lux and a relative humidity of 70%. During the germinating phase of 4 to 5 days, the pots are covered with lightpermeable material and watered with deionised water to increase the local humidity. After the 5th day, 0.5% of a commercial liquid fertilizer (Geenzit ®) is added to the water. The test is evaluated 12 days after sowing and the action on the plants is assessed according to the following rating:

| 1 | plants have not emerged or are totally withered |
| 2-3 | very pronounced action |
| 4-6 | medium action |
| 7-8 | weak action |
| 9 | no action (as untreated controls). |

Preemergence action:

Concentration of the test compound emulsion: 70.8 ppm

| Test plant Compound | Nasturtium | Stellaria | Agrostis | Digitaria |
|---|---|---|---|---|
| 1.1 | 2 | — | — | — |
| 1.5 | 1 | 2 | 1 | 1 |
| 1.6 | 2 | 2 | 2 | 2 |

—: not tested

EXAMPLE 7

Postemergence herbicidal action (contact action)

A large number of weeds and cultivated plants, both monocots and dicots, are sprayed postemergence in the 4- to 6-leaf stage with an aqueous dispersion of test compound at a rate of application of 4 kg a.i./ha, and then kept at 24°-26° C. and 45-60% relative humidity. The test is evaluated 15 days after treatment. The plants treated with compounds of formula I in this test exhibit pronounced irreversible damage.

EXAMPLE 8

Growth inhibition of tropical cover crops

The test plants (*centrosema plumieri* and *centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 9

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 6 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

EXAMPLE 10

Growth inhibition of cereals

Summar barley (*Hordeum vulgare*) and summer rye (Secale) are sown in sterilised soil in plastic beakers in a greenhouse and watered as required. The cereal shoots are treated about 21 days after sowing with an aqueous spray mixtures of a compound of the formula I. The concentration corresponds to 100 g of active ingredient per hectare. Evaluation of the growth of the cereals is made 21 days after application. A comparison with untreated controls shows that the growth of cereal plants treated with compounds of the formula I is significantly reduced (60-90% of the controls) and that the diameter of the stalks has in some cases increased.

EXAMPLE 11

Growth inhibition of grasses

Seeds of the grasses *Lolium perenne, Poa pratensis, Festuca ovina,* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

What is claimed is:

1. An N-azidophenylsulfonyl-N'-pyrimidinyl urea of the formula I

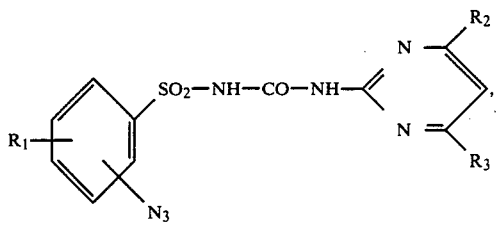

wherein
$R_1$ is hydrogen, halogen, nitro, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy,
$R_2$ is $C_1$-$C_3$alkyl, $C_1$-$C_3$alkoxy or $C_1$-$C_3$haloalkoxy,
$R_3$ is hydrogen, halogen, $C_1$-$C_3$alkyl, $C_1$-$C_3$haloalkyl, $C_1$-$C_3$alkoxy, $C_1$-$C_3$haloalkoxy, $C_2$-$C_5$alkoxyalkoxy or —$NR_4R_5$, wherein
$R_4$ is hydrogen or methyl and
$R_5$ is hydrogen, methyl, ethyl or methoxy,
or a salt thereof.

2. A compound according to claim 1, wherein the azido radical is in the 2-position to the sulfonyl group.

3. A compound according to claim 1, wherein $R_1$ is hydrogen.

4. A compound according to claim 1, wherein $R_2$ and $R_3$ together contain not more than 3 carbon atoms.

5. A compound according to claim 1, wherein $R_2$ and $R_3$ are selected from the group consisting of methyl, methoxy, dimethylamino, difluoromethoxy and 2,2,2-trifluoroethoxy.

6. A compound according to claim 1, wherein $R_1$ is $C_1$-$C_4$alkoxycarbonyl.

7. A compound according to claim 6, wherein $R_1$ is in the 2-position to the sulfonyl group and $R_2$ and $R_3$ are selected from the group consisting of methyl, methoxy, difluoromethoxy, dimethylamino and 2,2,2-trifluoroethoxy and together contain not more than 3 carbon atoms.

8. A compound according to claim 7, wherein $R_2$ and $R_3$ are methyl, methoxy or difluoromethoxy.

9. N-(2-Methoxycarbonyl-5-azidophenylsulfonyl)-N'-(4-difluoromethoxy-6-methylpyrimidin-2-yl)urea according to claim 8.

10. N-(2-Azidophenylsulfonyl)-N'-(4-methoxy-6-methylpyrimidin-2-yl)-urea according to claim 3.

11. N-azidophenylsulfonyl-N'-(4,6-dimethoxypyrimidin-2-yl)urea according to claim 3.

12. A herbicidal and plant growth regulating composition which contains an effective amount of at least one N-phenylsulfonyl-N'-pyrimidinyl-urea of the formula I as claimed in claim 1, together with a carrier and/or other adjuvants.

13. A method of controlling undesired plant growth, which comprises applying an effective amount of a N-phenylsulfonyl-N'-pyrimidinylurea of the formula I according to claim 1, or of a composition containing such a compound to the plant or the locus thereof.

14. A method of inhibiting plant growth, which comprises applying an effective amount of a N-phenylsulfonyl-N'-pyrimidinylurea of the formula I according to claim 1 to the plant or the locus thereof.

15. A method according to claim 13 of selectively controlling weeds pre- or postemergence in crops of useful plants, which method comprises applying thereto a N'-phenylsulfonyl-N'-pyrimidinylurea of the formula I.

16. A method according to claim 14 of inhibiting plant growth beyond the 2-leaf stage preemergence, which method comprises applying thereto a N-phenylsulfonyl-N'-pyrimidinylurea of the formula I.

17. A method according to claim 15, wherein the crops of useful plants are sugar cane, cereals, maize, rice, soybeans and cotton.

18. A method of reulating the growth of cultivated plants to obtain an increase in yield, which comprises applying thereto an effective amount of a 'N'-phenylsulfonyl-N'-pyrimidinylurea of the formula I as claimed in claim 1 to the plant or the locus thereof.

19. A method according to claim 18, wherein the cultivated plants are soybeans.

20. A method according to claim 14 wherein the plants are cover crop leguminosae.

* * * * *